United States Patent
Panescu et al.

(10) Patent No.: US 8,019,419 B1
(45) Date of Patent: Sep. 13, 2011

(54) METHODS AND APPARATUS FOR LEADLESS, BATTERY-LESS, WIRELESS STIMULATION OF TISSUE

(76) Inventors: Dorin Panescu, San Jose, CA (US); Ojas A. Buch, Valencia, CA (US)

(*) Notice: Subject to any disclaimer, the term of this patent is extended or adjusted under 35 U.S.C. 154(b) by 295 days.

(21) Appl. No.: 12/284,789

(22) Filed: Sep. 24, 2008

Related U.S. Application Data

(60) Provisional application No. 60/995,020, filed on Sep. 25, 2007.

(51) Int. Cl.
*A61N 1/05* (2006.01)
(52) U.S. Cl. .................................................. 607/33
(58) Field of Classification Search ............... 607/9, 33, 607/60, 61
See application file for complete search history.

(56) References Cited

U.S. PATENT DOCUMENTS

| | | | | |
|---|---|---|---|---|
| 4,524,774 A * | 6/1985 | Hildebrandt | | 607/62 |
| 5,313,953 A * | 5/1994 | Yomtov et al. | | 600/508 |
| 5,411,535 A * | 5/1995 | Fujii et al. | | 607/32 |
| 5,814,089 A * | 9/1998 | Stokes et al. | | 607/32 |
| 6,061,596 A * | 5/2000 | Richmond et al. | | 607/41 |
| 6,141,588 A * | 10/2000 | Cox et al. | | 607/9 |
| 7,203,548 B2 * | 4/2007 | Whitehurst et al. | | 607/39 |
| 7,236,821 B2 * | 6/2007 | Cates et al. | | 607/2 |
| 7,295,879 B2 * | 11/2007 | Denker et al. | | 607/61 |
| 7,519,421 B2 * | 4/2009 | Denker et al. | | 607/5 |
| 7,532,933 B2 * | 5/2009 | Hastings et al. | | 607/33 |
| 7,647,109 B2 * | 1/2010 | Hastings et al. | | 607/32 |
| 7,743,151 B2 * | 6/2010 | Vallapureddy et al. | | 709/227 |
| 2002/0128546 A1 * | 9/2002 | Silver | | 600/365 |
| 2010/0125312 A1 * | 5/2010 | Stevenson et al. | | 607/45 |

* cited by examiner

Primary Examiner — Brian T Gedeon

(57) ABSTRACT

A system is disclosed for stimulating body tissue includes one or more leadless, battery-less, implantable electrodes; and an external controller configured to transmit energy to the implantable electrode(s) via an RF signal for generating tissue stimulating pulses emitted by the respective electrode(s). The external controller is preferably further configured to transmit identification information to the implantable electrode(s) for secured information exchange. The one or more implantable electrodes are preferably each configured to transmit sensed tissue information to the external controller via an RF signal. The system may employ fixation technologies such as screw-in mechanisms, stent-like scaffolding, cuff-type or anchoring mechanisms in order to attach the implanted electrode(s) to respective target body tissues, such as (without limitation) cardiac tissue, brain tissue, bladder tissue, diaphragm, nerve tissue, spine, digestive tract tissue, and muscle tissue.

21 Claims, 3 Drawing Sheets

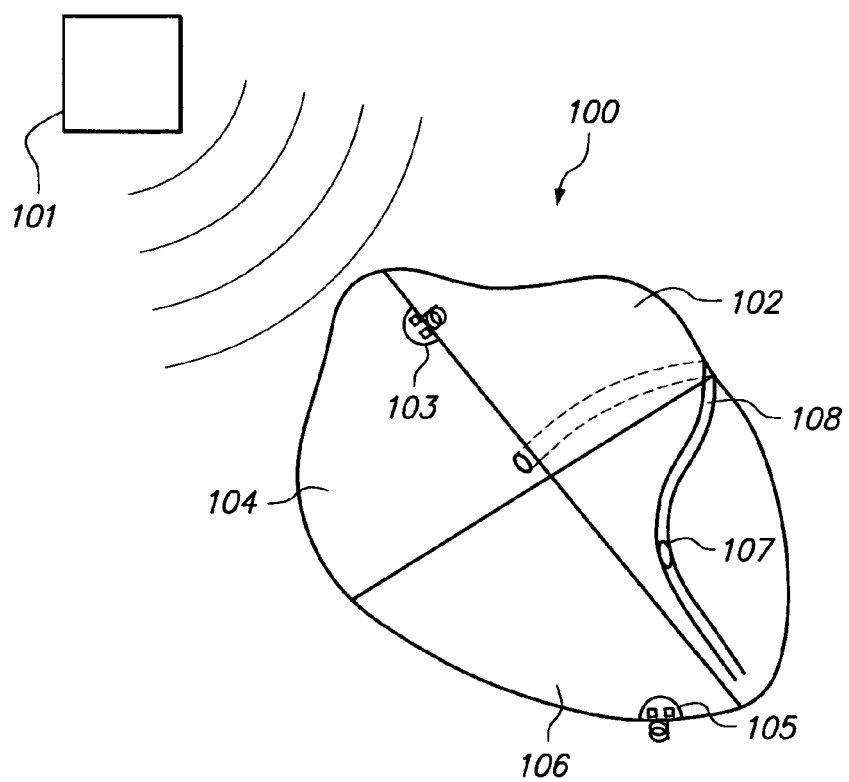
FIG. 1
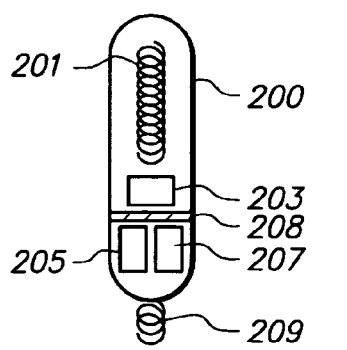 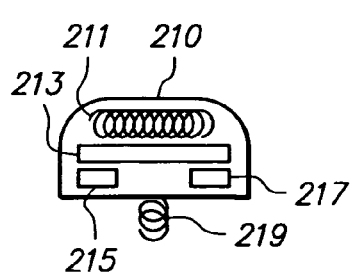 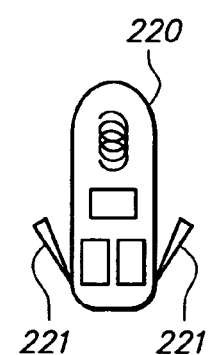
FIG. 2A  FIG. 2B  FIG. 2C

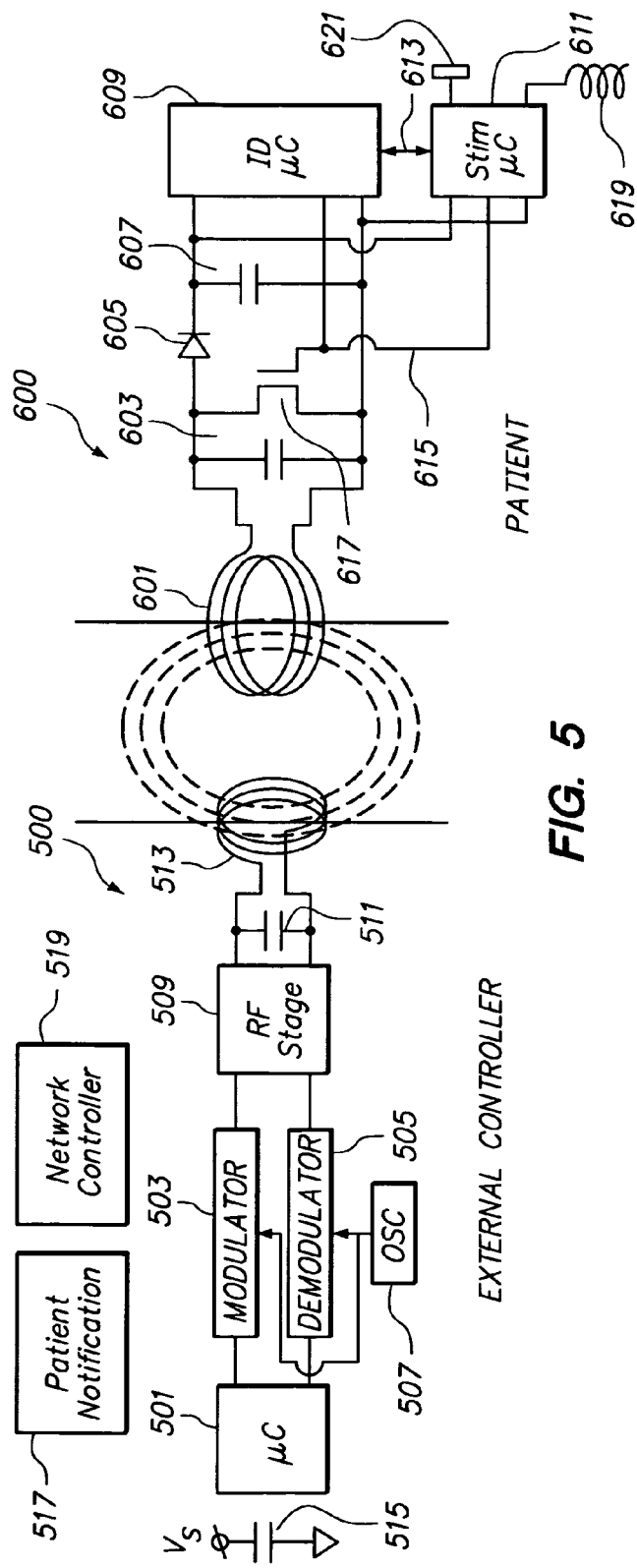
FIG. 5
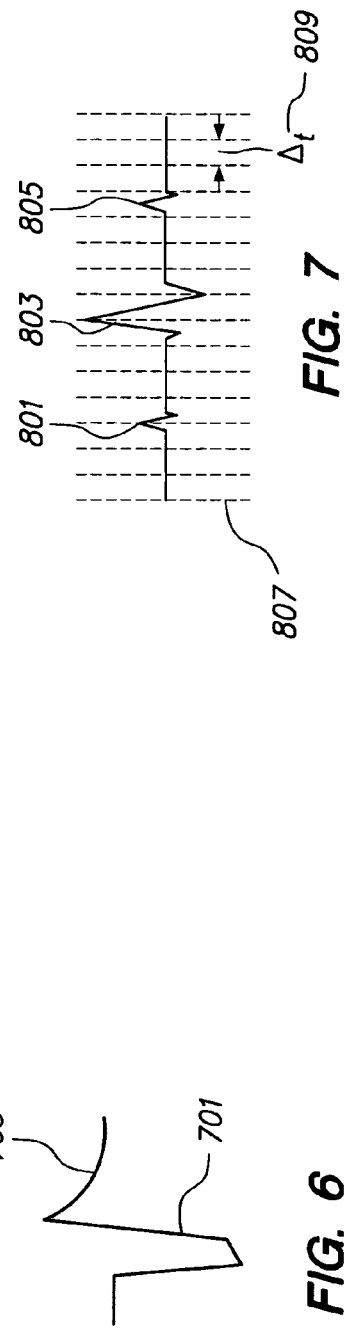
FIG. 6
FIG. 7

METHODS AND APPARATUS FOR LEADLESS, BATTERY-LESS, WIRELESS STIMULATION OF TISSUE

RELATED APPLICATION DATA

This application claims the benefit under 35 U.S.C. §119 of U.S. Provisional Application No. 60/995,020, filed Sep. 25, 2007, the contents of which are fully incorporated herein.

FIELD

The disclosed inventions pertain to the field of tissue stimulation devices, and in particular to leadless, wireless tissue stimulation devices and methods of their use.

BACKGROUND

Current technologies used for long-term tissue stimulation employ electrodes, leads and devices, all of which being implantable. For example, in order to stimulate cardiac tissue for treatment of bradycardia, implantable pacemaker systems use up to three electrodes deployed in the heart via appropriate leads. The leads connect to the header of the pacemaker can, which is implanted, typically, in a skin pocket located in the left or right chest. The leads are threaded through a vein, typically a subclavian vein, into the superior vena cava. Depending on the pacemaker configuration, one lead and its electrode are positioned in the high right atrium, a second lead in the right ventricle, and a third lead, if used, in one of the coronary sinus branches that extends over the epicardial aspect of the left ventricle. The pacemaker can carries a set of integrated circuits and a battery. Given the low power consumption of its electronic circuits, a typical pacemaker is expected to last between 7-10 years, after which the battery typically has been depleted. The patient would have to undergo a surgery to have the pacemaker replaced.

While highly effective in treating bradycardia, implantable pacemakers can have adverse effects, mostly related to lead fractures, infections of the skin pocket, premature battery depletion, software upgrades, etc. Particularly, in older patient population the leads can cause significant wear and tear of neighboring tissue layers. Similarly, the skin pocket associated with the pacemaker can is, in certain patient populations, very prone to infections, edema or hematoma. If the battery depletes sooner than expected, the patient would have to be exposed to early surgery to have the device replaced. In case of problems with the software that runs inside the pacemaker, patients may also have to undergo surgery to have the device replaced (certain pacemaker models still run their code from ROM memory, rather than RAM, which makes it very problematic to perform software upgrades without resorting to device replacement via surgery).

In recent years, given the large number of older patients that wear pacemakers, compatibility with magnetic resonance imaging (MRI) systems has become desired. It is important to note that even the modern pacemaker models do not perform their functions per specifications when the patient is placed in the vicinity of MRI equipment. In most cases, the pacemaker has to be turned off. If the patient is pacemaker-dependent special solutions have to be employed to keep their heart paced during the MM procedure. Additionally, the MRI fields can generate significant heating in the leads or around the can. Such heating can cause inadvertent thermal tissue damage.

Implantable stimulator systems are currently used for many other applications. Stimulation of the nerves system is, for example, another area of application. Patients may wear devices that perform spine stimulation, vagus nerve stimulation or brain stimulation. All such devices currently on the market use leads to connect the stimulating electrodes to the controller that drives them.

SUMMARY

Embodiments of the disclosed inventions employ radiofrequency (RF) fields to transfer signals between a controller unit that is external to a patient's body, and one or more implanted leadless, battery-less electrodes. RF signals transferred between the external controller unit and the implanted electrode(s) are used (by way of non-limiting examples) to identify electrode(s), to initiate and terminate stimulation, and to transfer sensed information from the electrode(s) to the controller. Thus, the system advantageously eliminates the need for leads and for skin pockets. And, since the controller is external to the body, software upgrades can be easily implemented. Additionally, the controller can be designed using materials and techniques that make the system MRI compatible. Although most of the disclosed and described embodiments are directed to cardiac pacemaker applications, embodiments of the disclosed inventions may also be used for leadless, wireless systems for other fields, such as for neurostimulation, brain stimulation, gastric stimulation, or bladder stimulation, etc.

In one embodiment, a system for stimulating tissue comprises at least one leadless battery-less implanted electrode that incorporates an RF signal processor, and an external unit that incorporates a second RF signal processor, wherein the external unit controls the second RF signal processor to send energy to the at least one implanted electrode and control the generation of tissue stimulating pulses by the at least one implanted electrode. By way of non-limiting examples, identification information may be sent by the external unit to the at least one implanted electrode, and the at least one implanted electrode may process and transmit tissue sensed information to the external unit. In various embodiments, the RF signal may be amplitude, frequency, or phase modulated. In various embodiments, the at least one implanted electrode is affixed to tissue using one or more of a screw-in mechanism, a stent-like scaffolding, a cuff-type mechanism, and tissue using anchoring tins. The implanted electrode(s) may be affixed to a number of different tissue sites to be stimulated, such as cardiac tissue, brain tissue, bladder tissue, diaphragm tissue, the vagus nerve, spine tissue, digestive tract tissue, and motor muscle tissue. In some embodiments, the external unit is attached to the patient.

In one embodiment, a system for stimulating cardiac tissue includes a first leadless, battery-less electrode that incorporates a first RF signal processor and is configured for implantation in a patient's right atrium, a second leadless, battery-less electrode that incorporates a second RF signal processor and is configured for implantation in the patient's right ventricle, and an external unit that incorporates a third RF signal processor, wherein the external unit controls the second RF signal processor to send energy to the first and second implanted electrodes and to control the generation of tissue stimulating pulses by the implanted electrodes. The system may further include a third leadless, battery-less electrode that incorporates its own RF signal processor and is configured for implantation in the coronary sinus, wherein the external unit controls the timing of stimulating pulses generated by all three implanted electrodes in order to implement cardiac resynchronization therapy in the patient. The electrodes may be unipolar or bipolar, and preferably process and transmit tissue sensed information to the external unit. The external unit may exchange identification information with the implanted electrodes, and may alert the patient if certain conditions are met. The external unit may be configured to send information over a telecommunication network.

In one embodiment, a method of stimulating tissue includes the acts of sending energy from an external unit to at least one battery-less, leadless implanted electrode; and controlling the generation of tissue stimulating pulses by the at least one implanted electrode from the external unit. In such embodiments, identification information may be sent by the external unit to the at least one implanted electrode, and the at least one implanted electrode processes and transmits tissue sensed information to the external unit.

Other and further embodiments and aspects of the disclosed inventions will become apparent from the following detailed description, when read in view of the accompanying drawings.

BRIEF DESCRIPTION OF THE DRAWINGS

Referring now to the drawings, in which like reference numbers represent corresponding components or patient anatomy in the various embodiments:

FIG. 1 is a schematic depiction of one embodiment of a leadless, wireless tissue-stimulation system shown employed as a cardiac pacing stimulation system;

FIGS. 2a-2d are embodiments of an implantable electrode for use in the system of FIG. 1, each including a schematic representation of the associated RF signal transceiver circuitry and tissue stimulation pulse generator in a biocompatible, encapsulated within a hermetically sealed electrode casing, and each having differing tissue attachment mechanisms;

FIG. 5 is a block functional diagram of the system of FIG. 1;

FIG. 6 depicts an exemplary tissue-stimulating pulse that can be generated by stimulation controller of the system of FIG. 1; and FIG. 7 depicts a typical sensed signal from cardiac tissue shown in relation to signal-acquisition sampling intervals when using the system of FIG. 1.

DETAILED DESCRIPTION OF THE ILLUSTRATED EMBODIMENTS

Figure 2D:
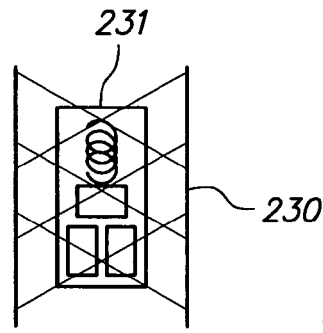

FIG. 1 depicts an exemplary embodiment of system designed according to the disclosed inventions. While the embodiment of FIG. 1 is directed to a pacemaker, this is for purposes of illustration only, and should not be construed as a limitation of the disclosed inventions, and to the contrary, those skilled in the art can readily apply the techniques, methods and concept disclosed herein in other diagnostic and/or therapeutic applications and fields of medicine.

With reference to FIG. 1, an external controller 101 periodically generates a RF electromagnetic field that reaches to electrodes 103, 105 and 107, which are implanted at respective locations in a patient's right atrium (RA) 104, right ventricle (RV) 106, and coronary sinus (CS) left ventricular (LV) branch 108. The RF field created by the external controller 101 serves several purposes, including delivering the energy required for operating respective electronics located inside the electrodes 103, 105 and 107. The external controller 101 also transmits unique identification codes that identify a particular electrode to be activated out of the three electrodes (again, the actual number of electrodes may be different than three, especially in the case of different applications), and preferably also transmits information confirming that the identification codes of the respective electrodes are uniquely linked to the identification of the external controller to avoid activating another patient's electrodes should such another patient be in proximity to the external controller. The "confirmation" is also preferred for security purposes, such as for prevention of system hacking. Once the identification communication completes successfully, the RF field transfers information to the selected electrode that enables it to deliver an electrical stimulus to underlying tissue.

The parameters of the pacing stimulus can be hard-wired in the electronics or can be programmable via the RF field. Additionally, once the identification has been completed successfully, the RF field transfers information that allows the selected electrode to communicate sensed signals back to the controller. By way of non-limiting example, electrode 103 can sense and send back to the controller RA electro-gram (EGM) data, electrode 105 can sense and send back RV EGM data, and electrode 107 can transfer epicardial LV EGM data.

The system hardware and software preferably trigger RF field and transfer events at rates that are frequent enough to support the power consumption of the implanted circuits and the transfer of information that is of digital (e.g. ID codes) or of analog (e.g. sensed physiological signals such as EGMs) nature. As such, the RF fields may be pulsed or continuous, and may also be modulated by transferred information. Such modulation could be in any of the known variants, such as, but not limited to: amplitude, frequency, phase, or code modulation, etc. In order to support the functions above, the implanted electrodes are associated with circuits or blocks as shown in FIG. 2.

FIG. 2a shows an implantable electrode, constructed according to one embodiment, which encapsulates the associated circuit in a biocompatible, hermetically sealed encasing 200. Electrode 209 has a corkscrew profile and can be screwed into tissue using suitable delivery tools, such as introducers, stylets and sheaths. Embedded antenna 201 receives or emits RF fields. RF module 203 contains a demodulator that feeds into a capacitor that temporarily stores the energy required to operate all embedded circuits. RF module 203 also contains a transceiver that works together with the antenna 201 to carry the RF field communication. The information processed by 203 is then sent to the identification processor 207, which confirms that the ID code received from the external controller is associated with the correct external controller and does not come from another nearby unit, or from an interference source. If a match does not occur then the operation discontinues until another ID confirmation phase is initiated by the external controller.

The identification processor 207 preferably also matches the electrode ID code sent by the external controller with its own ID code. If a match occurs then operation continues, as the electrode ID processor has confirmed that it was selected for communication with the external controller. If the match fails, indicating that a different electrode has been selected, the communication stops until another ID confirmation phase is initiated by the external unit. If the ID confirmation succeeds then the local stimulation controller 205 becomes enabled. Upon becoming enabled, the controller 205 prepares itself for issuing stimulation pulses. For example, if electrode 200 is used within a cardiac pacemaker system then controller 205 issues a stimulus that can capture the heart. Such stimulus, typically, has amplitudes between 0.2 and 10 V and durations between 0.1 to 10 ms. The pacing stimulus can be uni-polar, with respect to a reference electrode that could be, for example, associated with the external controller. Alternatively, the pacing stimulus could be bipolar between electrode 209 (typically the cathode) and a ring electrode 208 (typically the anode), located externally to the encasing 200.

The energy required by the pacing pulse comes from the energy-storing capacitor that is connected to the RF module, as discussed above. For other applications, such as muscle, brain, gastric, spine, nerve or bladder stimulation, the amplitude and duration of the stimulus are chosen in accordance with the strength-duration curves associated with the respective tissues. For example, nerves have a much faster response time. Consequently, stimuli tailored for nerves' response time would have durations in the 10-100 microsecond range and amplitudes that may range from mV to several V levels. Although not required, in an alternate embodiment, in addition to generating stimuli, controller 205 may also be responsible for acquiring sensed signals.

For example, for a cardiac pacemaker application, controller 205 acquires the EGM that corresponds to the chamber in which electrode 200 is implanted. The EGM could be unipolar, with respect to a reference electrode that could be, for example, associated with the external controller. Alternatively, the EGM could be bipolar and acquired between stimulating electrode 209 and a ring electrode 208, located externally to the encasing 200. Although only two electrodes are shown in FIG. 2, the scope of the disclosed inventions is not so limited and covers implantable electrode bodies 200 that may carry more than two electrodes. Depending on the part of the heart or on the particular application, other anchoring techniques could be employed.

FIG. 2b shows another embodiment of encasing 210 that carries a screw-in type tip electrode, including (within the electrode body—shown schematically) the antenna 211, RF module 213, ID processor 217 and stimulation controller 215. Alternatively, the encasing 220 may be anchored with fins 221. Applications such as spine or bladder stimulation may find the fins 221 (shown in FIG. 2c) as a preferred anchoring mechanism. For pacemakers that include the cardiac resynchronization therapy (CRT) option, i.e., those with electrodes implanted in the RA, RV and CS, the anchoring mechanism shown in FIG. 2d might be more suitable. In particular, a stent-type scaffolding 230 encloses the encasing 231 that hosts the electronics described above. The scaffolding carrier 230 could be deployed in manners similar to those used in angioplasty for stent deployed, by using sheath, introducers and balloon catheters.

Figure 3:
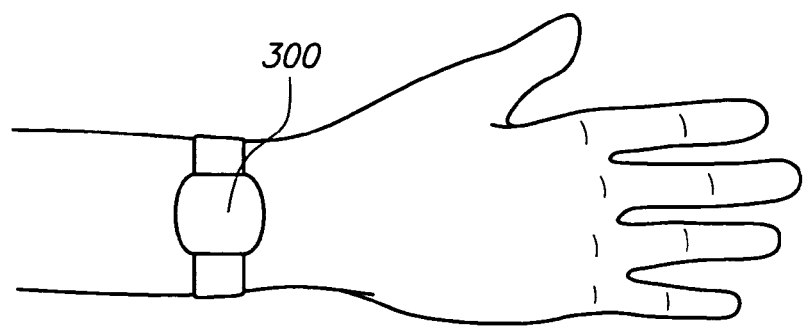
FIG. 3 illustrates one simplified embodiment of an external controller for use in the system of FIG. 1, wherein the controller is mounted as a wrist-watch on the patient's hand.
Figure 4A:
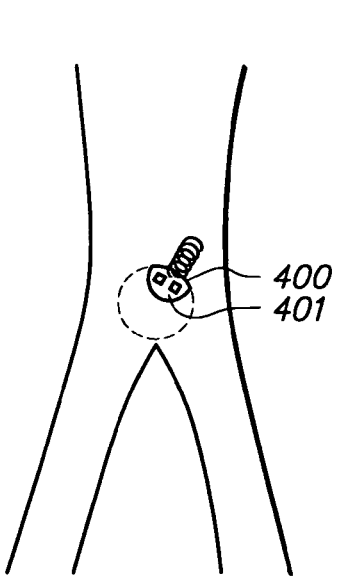
FIG. 4a depicts a simplified alternate embodiment, in which the implantable electrode is attached to bladder tissue.
Figure 4B:
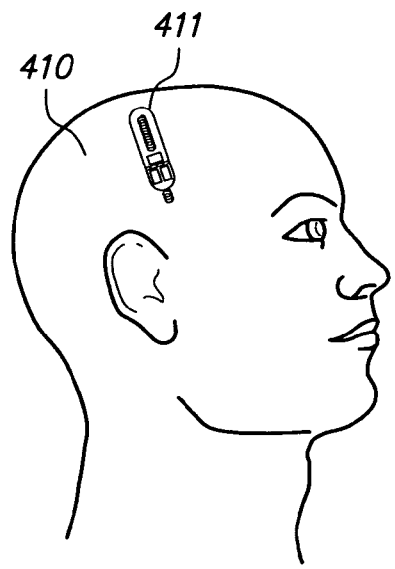
FIG. 4b depicts a simplified alternate embodiment, in which the implantable electrode is attached to brain tissue.

FIG. 3 shows a preferred embodiment wherein the external controller 300 is mounted as a wrist-watch on the patients' hand. Given that, in the example above, controller 300 performs critical cardiac stimulation functions, it is preferred to have attached in a permanent mount onto the patient's hand. Obviously, the permanent mount should be detachable if appropriate tools are used. For example, the wrist-band would have to be detached when the controller batteries are replaced. While FIG. 1 shows an application in the field of cardiology, FIGS. 4a and 4b describe implantation locations associated with bladder and brain stimulation, respectively. In either of these embodiments, controller 300 could be placed on the patient's hand.

FIG. 5 provides a detailed block diagram of the system. The external stimulator unit is driven by a microcontroller 501 that runs the software specific to the application. In a pacemaker embodiment, microcontroller 501 drives the signals for specific sequence of activation of pacing electrodes described in FIG. 1. Additionally, more complex pacing schemes could also reside in 501. The microcontroller has available memory that can be of either ROM or RAM, or both types. Typically, the application code can reside in ROM, or can be uploaded from ROM in RAM for a faster execution. Specific constants, such as calibration coefficients, can also reside in ROM and ported into RAM to interact with the code. Alternatively, microcontroller 501 can be RAM-only. The RAM-only variety offers most flexibility in case of code upgrades. The code can be programmed in RAM at initial procedure time and run for the life of the battery. Microcontroller 501 also runs the identification processes required to correctly ID the electrodes intended to trigger pacing stimuli. Microcontroller 501 interacts with modulator 503 and demodulator 505 for data transfer purposes. The modulator and demodulator are working based on an RF carrier frequency established by oscillator 507. The modulator and demodulator connect to the RF stage, which drives the inductor-capacitor (LC—513 and 511, respectively) circuit. In one embodiment, the output LC circuit may be tuned on the frequency designated as the communication carrier. The RF field is generated via inductor 513 (the system antenna) and propagates to the implanted electrodes inside the patient's body. Various modulation techniques may be employed in order to transmit and receive the RF field appropriately. For example, amplitude modulation offers electronics simplification, frequency modulation offers better signal to noise ration. Other techniques, such as shift frequency key, code modulation, phase modulation, etc., could be as effectively employed.

All blocks in the design are powered from the same battery 515. Given that the battery could be changed more frequently than for standard implantable stimulating device (i.e. every year could be feasible) the microcontroller can run advanced features that would typically pose a computing resource drain. For example, the microcontroller could run advanced implantations of CRT code. Additionally, the microcontroller could store larger amounts of signals or information received from the implanted electrodes. Unlike for implantable pacemakers, the external controller does not have a severe limitation of battery life or memory capacity. It is estimated that the memory capacity can easily exceed 10 MB, allowing not only for advanced code features, but also for more storage of sensed events associated with conditions the patient may have experienced. The electronics in FIG. 5, the patient side, could be implemented within each of the stimulating electrodes 600. Electrodes 600 (shown in FIG. 5) correspond to electrodes 103, 105 or 107 shown in FIG. 1, or to electrode 401, in FIG. 4a, or to 411, in FIG. 4b. The RF field set out by the microcontroller 501 is received by an antenna 601 incorporated inside electrode 600. The circuit formed by antenna 601 and capacitor 603 is preferably tuned on the RF field carrier frequency. The amplitude of the RF carrier is demodulated to provide operating power to the electrode electronics. For example, the demodulator can be formed by a diode 605 and a capacitor 607. A capacitor 607, referred to in the text above as energy-storing capacitor, stores the energy required for operation. Depending on operation complexity, capacitor 607 can be charged via the RF field continuously or periodically. For example, if the power consumption is low, then external controller 500 needs to send out refreshing bursts of RF field less frequently. Conversely, if the operation complexity is high, resulting in increased power consumption, then the refreshing bursts of RF field should be sent more frequently or continuously. The voltage developed on capacitor 607 supplies the ID processor 609 and the stimulation controller 611.

Stimulation controller 611 is connected to electrodes 619 and 621 that can be used for stimulation, sensing or both. The ID and stimulation controllers can exchange information over bus 613. For example, if the ID matching step passed successfully, the ID processor 609 can enable operation of stimulation controller 611. In an alternative embodiment, the ID processor 609 may also decode information needed to program stimulation parameters within stimulation controller 611. In same or another alternative embodiment, stimulation controller 611 may acquire sense information from electrodes 619 and 621 and pass it back to the ID processor 609 to be encoded for transmission back to the external controller 500. In order to communicate back with the external controller 500, the ID processor drives a modulator that modulates the RF field carrier which is transmitted back to the external controller 500 by the antenna 601 and its resonant capacitor 603. For example, the modulator can be implemented using a MOS transistor 617 that 'chops' the RF carrier voltage developing on capacitor 603. Under such scenario, the RF carrier could be modulated in amplitude, if transistor 617 drives the depth of RF carrier chopping. Alternatively, if transistor 617 changes the frequency at which it chops the RF carrier then the modulation could be conceived as frequency modulation. Although these two modulation schemes are presented as an example, without limitation, other modulation schemes could be employed as well. In another alternative embodiment, stimulation controller 611 can also communicate back to the external controller 500 by driving the modulator via bus 615. The modulator could be the same as or different than for ID processor 609. The ID codes required for security and for successful operation can be stored inside ID processor 609. Alternatively, these codes can reside in a memory chips associated with electrode 600. This memory chip could be accessed by either the ID processor 609 or by the stimulation controller 611.

FIG. 6 shows a typical pacing pulse that can be generated by stimulation controller 611. The pulse has a negative cathodal stimulation phase 701 followed by a positive anodal charge balancing phase 703. The amplitude of the phase 701 is expected to be as high as required for successful stimulation. For example, this amplitude could reach up to 10 V. The width of the phase 701 can be anywhere between a fraction of a millisecond up to several milliseconds. As an example, it is known that a pulse width of between 0.1 to 10 ms is sufficient to capture cardiac tissue. Other tissues would require different amplitudes or pulse durations. It is known that nerves can be captured with pulse amplitude in the range of millivolt to several volt and durations between a few tens to a few hundreds of microseconds. The charge balancing phase 703 is required to make sure that there is no net flow of current into tissue and for keeping the chemistry of the electrode metal stable.

FIG. 7 shows a typical sensed signal from cardiac tissue. There may be three distinct phases of activity. Phase 801, the P wave, reflects the atrial activity. Phase 803, the R wave, reflects the ventricular depolarization. Phase 805, the T wave, indicates the ventricular repolarization. Depending on the exact placement of electrodes, there may be additional or fewer phases seen in a typical cardiac response. These phases are sensed by the stimulation controller 611 and sent back to the external unit 500. The external unit 500 can decide pacing parameters based on these phase or detect occurrence of various arrhythmic events. Appropriate pacing maneuvers could be triggered in response to arrhythmia detection to attempt termination of such events.

In an alternative embodiment, sensed tissue information received from electrodes 103, 105 and 107 in FIG. 1 can be used to detect the progression towards heart failure. The sense information could, for example, be related to the electrical impedance detected by such electrodes. The electrical impedance could be measured by injecting currents into the thoracic or heart space from the above electrodes and then measure the resulting voltage with the same electrodes or different electrodes from the set listed above. Impedance could then be computed by dividing voltage by current. Techniques known in the art could then be used to trend heart failure. Alternatively, the sense information could be represented by the duration, amplitude or relative timing of phase 801, 803 and 805. Whatever the particular sense information, it can then be used to control parameters for cardiac resynchronization therapy (CRT) of heart failure.

In another alternative embodiment, CRT parameters can be fixed, pre-programmed in the external controller 500. Also shown in FIG. 7 are sampling intervals 807. In order to acquire sense information, the cardiac signal would be sampled at frequent enough intervals. The sampling period 809 is generally computed based on Nyquist's theorem. For cardiac signals, sampling frequencies are in the range of a few hundred to a few thousand Hertz. The exact sampling frequency plays a role in deciding how often the refreshing bursts of RF field have to be emitted. The frequency of these bursts has to be high enough to sustain the power consumption required by the sampling of the sense information. Although the embodiments above are presented for cardiac tissue applications, applications for other tissue are herein incorporated as well. For example, stimulation controller 611 could sense the response of nerves to stimulation. As nerves may respond faster, with higher frequency content, the sampling frequency would be higher as well. Muscle response, such as in the case of bladder stimulation, could also be checked to confirm optimal countenance control.

For pain management applications, the external controller 500 can drive a multitude of leadless, wireless electrodes 600 distributed at required locations along the spine. The electrodes 600 can provide required stimuli and sense response information that is sent back to the external controller for processing. Similar embodiments can be implemented for functional electrical stimulation (FES). Other applications of the system described herein, without any particular limitations, are: diaphragm stimulation, brain stimulation, stomach or digestive tract stimulation, muscular or limb stimulation, vagus nerve stimulation.

As it is important to inform the patient or the medical staff about the patient conditions as soon as possible, in one preferred embodiment the external unit 500 includes a patient notification block 517 that can alarm the patient under certain circumstances. Unit 500 can also include a network controller 519 that can connect to an information network in a wireless or wired fashion. For example, controller 519 can connect unit 500 to the Internet or to an intranet. Alternatively, it can provide Bluetooth™ or Zigbee™ communication features to connect to other compatible devices in such networks. If connected to a network, controller 519 can facilitate information exchange between unit 500 and a database, or, simply, send alert information to medical personnel.

Although particular embodiments of the disclosed inventions have been shown and described herein, it should be understood that the above discussion is for purposes of illustration and is not intended to be limiting. Various changes and modifications may be made without departing from the scope of the illustrated embodiments, and the disclosed inventions are limited only by the scope of the appended claims and equivalents thereof.

What is claimed is:

1. A system for stimulating tissue, comprising:
   at least one leadless, battery-less, implantable subsystem, comprising
      an energy-storing component
      a plurality of electrodes coupled to the energy-storing component and configured for generating tissue stimulating pulses,
      and
      control means configured for recognizing a first unique identification code transmitted by a matching external controller and for controlling generation of the tissue stimulation pulses;
   and
   an external controller, comprising
      a first unique identification code which identifies the external controller;
      an RF stage configured to provide operating energy to the energy-storing component(s) of the at least one implantable subsystem;
      a control unit configured to initiate an identity confirmation phase in which the external controller transmits said first unique identification code to the at least one implanted subsystem;
   wherein, prior to allowing generation of the tissue stimulation pulses, the control means for the at least one implanted subsystem determine that the external controller is the matching external controller based on whether they recognize the transmitted first unique identification code.

2. The system of claim 1, wherein:
   the control means for the at least one subsystem are also configured to recognize a second identification code that identifies the subsystem;
   the matching external controller also comprises the said second subsystem identification code;
   the matching external controller transmits the second subsystem identification code to the implanted subsystem;
   and,
   wherein, prior to allowing generation of the tissue stimulation pulses, the control means for the at least one implanted subsystem determine that the implanted subsystem has been selected for operation by the external controller based on whether they recognize the transmitted said second subsystem identification code.

3. The system of claim 1, wherein the at least one implantable subsystem is configured to acquire tissue information and to transmit this tissue information to the external controller.

4. The system of claim 3, wherein the external controller commands the implantable subsystem to generate said tissue stimulating pulses at least partially in accordance with the said acquired tissue information.

5. The system of claim 1, the at least one implantable subsystem comprising a fixation mechanism configured for placing the electrodes in contact to tissue.

6. The system of claim 5, wherein the fixation mechanism is one of the following kinds: screw-in, stent-like scaffolding, cuff-type or anchoring tines.

7. The system of claim 1, the external controller configured for being attached to a patient.

8. The system of claim 1, wherein the external controller configured to communicate with other external systems or devices via a network of one of the following types: Internet, Bluetooth or Zigbee.

9. The system of claim 1, wherein the external controller is configured to alert the patient if certain conditions are met.

10. The system of claim 1, wherein the at least one subsystem is configured to stimulate tissues of the following kinds: cardiac, brain, bladder, diaphragm, vagus nerve, nerve, spine, digestive tract, or motor muscle.

11. A method for stimulating cardiac tissue of a patient, comprising:
   implanting a first leadless, battery-less subsystem at one location in a patient's heart;
   implanting a second leadless, battery-less subsystem at a second location in a patient's heart;
   transmitting energy from an external controller via RF fields to the respective first and second implanted subsystems;
   having the control unit of an external controller initiate an identity confirmation phase in which the external controller transmits its first unique identification code to the implanted subsystems;
   and,
   wherein, prior to allowing generation of the cardiac tissue stimulation pulses, the control means for the implanted subsystems determine that the external controller is the matching external controller based on whether they recognize the transmitted first unique identification code.

12. The method of claim 11, further comprising implanting and operating accordingly a third leadless, battery-less subsystem at a third location in a patient's heart.

13. The method of claim 11, wherein at least one of the implanted subsystems acquire and transmit sensed tissue information to the external controller.

14. The method of claim 13, wherein the external controller commands the implantable subsystem to generate said cardiac tissue stimulating pulses at least partially in accordance with the said acquired tissue information.

15. The method of claim 11, wherein, prior to allowing generation of the cardiac tissue stimulating pulses, the control means for the implanted subsystem determine that the respective implanted subsystem has been selected for operation by the matching external controller based on whether they recognize the corresponding said second subsystem identification code, as transmitted by the matching external controller.

16. A method of providing therapy to a patient, comprising:
   implanting in body tissue of a patient at least one leadless, battery-less, implantable subsystem, which comprises:
      an energy-storing component;
      a plurality of electrodes coupled to the energy-storing component and configured for generating tissue stimulating pulses;
      and,
      control means configured for recognizing a first unique identification code transmitted by a matching external controller and for controlling generation of the tissue stimulation pulses;
   transmitting energy from an external controller, which comprises:
      a first unique identification code which identifies the external controller;
      an RF stage configured to provide operating energy to the energy-storing component of the at least one implantable subsystem;
      a control unit initiating an identity confirmation phase in which the external controller transmits said first unique identification code to the at least one implanted subsystem;
   and,
   determining that the external controller is the matching external controller based on whether the control means for the at least one implanted subsystem recognize the first unique identification code transmitted by the external controller.

17. The method of claim 16, wherein the at least one implantable subsystem is acquiring tissue information and transmitting the information to an external controller.

18. The method of claim 17, wherein the external controller is commanding the implantable subsystem to generate said stimulating pulses at least partially in accordance with the said acquired tissue information.

19. The method of claim 16, wherein the external controller alerts the patient if certain conditions are met.

20. The method of claim 16, wherein the external controller communicates patient information to a medical provider via one of the following network types: Internet, Bluetooth or Zigbee.

21. The method of claim 16, wherein the at least one subsystem is implanted in tissues of the following kinds: cardiac, brain, bladder, diaphragm, vagus nerve, nerve, spine, digestive tract, or motor muscle.

* * * * *